US009603998B2

(12) United States Patent  
Geipel et al.

(10) Patent No.: US 9,603,998 B2  
(45) Date of Patent: Mar. 28, 2017

(54) MICRO-FLUIDIC CHAMBERS FOR USE IN LIQUID MEDICAMENT DELIVERY SYSTEMS

(75) Inventors: Andreas Geipel, Oftringen (CH); Christoph Huwiler, Baar (CH); Florian Kühni, Wabern (CH)

(73) Assignee: Roche Diagnostics International AG, Steinhausen (CH)

( * ) Notice: Subject to any disclaimer, the term of this patent is extended or adjusted under 35 U.S.C. 154(b) by 1282 days.

(21) Appl. No.: 12/877,569

(22) Filed: Sep. 8, 2010

(65) Prior Publication Data

US 2011/0066108 A1 Mar. 17, 2011

(30) Foreign Application Priority Data

Sep. 11, 2009 (EP) ..................... 09170095

(51) Int. Cl.  
*A61M 5/14* (2006.01)  
*A61M 5/168* (2006.01)  
(Continued)

(52) U.S. Cl.  
CPC ........ *A61M 5/16877* (2013.01); *A61M 5/141* (2013.01); *A61M 5/36* (2013.01);  
(Continued)

(58) Field of Classification Search  
CPC ...... A61M 5/16877; A61M 2205/0244; A61M 5/141; G01R 33/302  
(Continued)

(56) References Cited

U.S. PATENT DOCUMENTS 4,238,207 A * 12/1980 Ruschke ............. A61M 1/3627  
                                                           156/290  
5,439,587 A * 8/1995 Stankowski .......... A61M 5/165  
                                                          210/321.64  
(Continued)

FOREIGN PATENT DOCUMENTS

EP        0 718 016 A1    6/1996  
EP        1 818 664 A1    8/2007  
WO    2004/085063 A2   10/2004

OTHER PUBLICATIONS

European Search Report, completion date of Feb. 15, 2010 for European Application No. EP 09170095.5-2320, pp. 1-5.

(Continued)

*Primary Examiner* — Matthew F Desanto  
(74) *Attorney, Agent, or Firm* — Dinsmore & Shohl LLP (57) ABSTRACT

Micro-fluidic chambers for use in a liquid medicament delivery system, include a bottom substrate and a top cover, the top cover being spaced from the bottom substrate so as to define a height of the chamber, wherein, one or more walls or fillings are positioned in the chamber, the walls or fillings defining a fluid channel there between such that the fluid channel extends from an inlet of the chamber to an outlet of the chamber, wherein, each of the walls or fillings has a height less than the height of the chamber so as to define a fluid gap between a top surface of each wall or filling and the top cover; and wherein, the dimensions of the walls or fillings and the chamber are such that the fluid gap will be filled with liquid by capillary forces via the fluid channel when liquid is introduced into the fluid chamber.

14 Claims, 7 Drawing Sheets

(51) Int. Cl.
*A61M 5/36* (2006.01)
*G01R 33/30* (2006.01)

(52) U.S. Cl.
CPC ............... *A61M 2205/0244* (2013.01); *A61M 2205/3331* (2013.01); *G01R 33/302* (2013.01); *Y10T 137/0318* (2015.04); *Y10T 137/8326* (2015.04); *Y10T 137/8593* (2015.04)

(58) Field of Classification Search
USPC ..... 604/890.1, 892.1, 891.1, 93.01, 122–126
See application file for complete search history.

(56) References Cited

U.S. PATENT DOCUMENTS

| | | | |
|---|---|---|---|
| 6,986,649 B2 | 1/2006 | Dai et al. | |
| 7,027,683 B2 | 4/2006 | O'Connor et al. | |
| 7,036,917 B2* | 5/2006 | Muller-Chorus | B01L 3/0241 347/84 |
| 7,254,008 B2* | 8/2007 | Xie | G01N 27/226 361/271 |
| 7,527,767 B2 | 5/2009 | Breimesser et al. | |
| 9,285,324 B2* | 3/2016 | Leuenberger Jockel | A61M 5/16854 |
| 2001/0021830 A1 | 9/2001 | Yamada et al. | |
| 2004/0094733 A1 | 5/2004 | Hower et al. | |
| 2005/0243500 A1 | 11/2005 | Xie et al. | |
| 2007/0028683 A1 | 2/2007 | Ionescu-Zanetti | |
| 2009/0064790 A1 | 3/2009 | Davidovits et al. | |
| 2009/0090172 A1 | 4/2009 | Angelescu et al. | |
| 2009/0151422 A1 | 6/2009 | Unger et al. | |
| 2009/0165876 A1* | 7/2009 | Atkin et al. | 137/825 |
| 2011/0045492 A1* | 2/2011 | Bau-Madsen | B01L 3/5027 435/7.1 |

OTHER PUBLICATIONS

Kohl, et al., "A microfluidic experimental platform with internal pressure measurements", 2005, pp. 212-221, Sensors and Actuators A 118.

Pagel, et al., "Microfluidic Systems in PCB Technology", 2005, pp. 2368-2371, IEEE.

* cited by examiner

MICRO-FLUIDIC CHAMBERS FOR USE IN LIQUID MEDICAMENT DELIVERY SYSTEMS

CROSS REFERENCE TO RELATED APPLICATIONS

This application claims priority to European Patent Application No. EP09170095.5 filed on Sep. 11, 2009, which is incorporated by reference herein.

TECHNICAL FIELD

This specification relates to micro-fluidic chambers for use in liquid medicament delivery systems, pressure sensors, degassing devices and infusion pump devices.

BACKGROUND

Devices for the automated release of liquid medicaments can be used with patients who have a continuous and/or, in the course of the day, a varying need of a medicine that can be administered by subcutaneous infusion. Specific applications include, for example, certain pain therapies and the treatment of diabetes. In such cases, computer controlled infusion pump devices may be used, which can be carried by the patient on the body, and which contain a certain amount of liquid medicament in a medicine reservoir. The medicine reservoir can comprise enough medicine sufficient for one or several days. Furthermore, the liquid medicament can be supplied to the patient's body from the medicine reservoir through an infusion cannula or an injection needle.

In self-administration of medicaments, such as, for example, insulin, the patients using the medicament in question and administering it themselves by means of an infusion pump device may seek convenience and discretion. As a consequence, the acceptable dimensions of such infusion pump devices may be limited in order not be evident through clothing and to be carried in a comfortable manner. In one type of infusion pump device, the liquid medicament may be obtained by a downstream pump from a flexible container. Flexible containers can comprise a smaller volume surplus of the container in relation to its content, which can reduce the manufacture costs and the achievable overall dimensions of an infusion pump device with such a flexible container.

However, infusion pump devices can include air bubbles in the fluidic system, particularly in the pump system, and in other components, such as the container. If air bubbles remain in the fluidic system, they may be administered instead of the liquid medicament. Also, due to the high compressibility of gases in relation to liquids such as water, the air can reduce the stiffness of the fluidic system, which may limit the potential detection of blockages or occlusions in the fluidic system when monitoring the fluidic pressure. Furthermore, fluidic systems can include dead volume which may not be emptied or drained completely. Thus, since a certain percentage of the liquid medicament inevitably remains in the fluid system and has to be disposed, the dead volume can increase the costs per dose and thus of the overall therapy costs.

Micro-fluidic chambers can be used, for example, as sensor chambers in pressure sensors for fluidic systems. Such pressure sensors can comprise a chamber filled with liquid that is fluidly connected to the fluidic system. The chamber can be covered by a flexible, resilient membrane, such that a pressure difference between the fluidic pressure inside the sensor chamber and the outside (atmospheric) pressure will temporarily deform the membrane. The resulting deflection of the membrane can then be measured to determine the internal pressure of the fluidic system.

One possible approach to measure the deformation of the membrane includes the optical detection of a light beam reflected by the membrane. Another possible approach can include capacitive sensing, in which the flexible, resilient membrane of the chamber acts as a capacitor electrode. When the membrane is deformed, the capacitance between the membrane capacitor electrode and a second capacitor electrode changes and is measured to determine the pressure difference acting on the membrane. Yet another possible approach to measure the deformation of the membrane is the use of strain gauges mounted to the membrane. In the context of liquid medicament administration via an infusion pump device, these exemplary pressure sensors, as well as alternative apparatuses and methods, may be used for controlling the dosing, monitoring the correct operation of the system, and detecting faults and hazards, such as occluded infusion lines or cannulae, empty containers, or malfunctioning pump systems. However, air bubbles in the in the micro-fluidic sensor chamber can reduce the stiffness of the fluidic system, and thus delay the response of the sensor to pressure changes in the fluidic system. The resulting irreproducible measurement errors may reduce the dosing accuracy of an infusion pump device, and increase the response time to an occlusion event.

Micro-fluidic chambers may also be employed as degassing devices for fluidic systems, particularly infusion pump devices, in which a liquid filled chamber may be covered by a gas-permeable membrane. Subject to the condition that there is a positive difference between the partial pressure of the gas present in the fluidic system and the pressure on the opposite side of the permeable membrane, gas, as bubbles or solved in the liquid, can leave the fluidic system by permeating through the membrane. In such uses, the properties of the micro-fluidic chamber and the performance of devices using such chambers may be independent on the orientation of the micro-fluidic chamber with respect to the gravity field, since the orientation of the device during application is undefined and may constantly change Thus, to limit or avoid air bubbles in the micro-fluidic chamber when the fluidic system is filled the first time, the so called priming of the system, the chamber may be filled in a controlled manner. However, the micro-fluidic chamber may comprise an uncontrolled orientation during this first filling procedure since the gravitation field leads to buoyancy forces that act on the air bubbles. Depending on the orientation and the design of the micro-fluidic chamber, air bubbles may be caught in certain areas of the chamber.

Accordingly, a need exists for alternative micro-fluidic chambers for use in liquid medicament delivery systems.

For the present specification the meaning of the term "air" shall not only include air as such, but any gas or composition of gases that may be present in a fluidic system, particularly pure nitrogen or other protective gases.

SUMMARY

In one embodiment, a micro-fluidic chamber for use in a liquid medicament delivery system, is provided. The micro-fluidic chamber includes a bottom substrate and a top cover, the top cover being spaced from the bottom substrate so as to define a height of the chamber. The one or more walls or fillings may be positioned in the chamber such that the walls or fillings define a fluid channel there between and such that the fluid channel extends from an inlet of the chamber to an outlet of the chamber. Each of the walls or fillings may have a height less than the height of the chamber so as to define a fluid gap between a top surface of each wall or filling and the top cover, and the dimensions of the walls or fillings and the chamber may be such that the fluid gap will be filled with liquid by capillary forces via the fluid channel when liquid is introduced into the fluid chamber.

In another embodiment, a method for delivering medicament to a patient is provided. The method comprises utilizing a liquid medicament delivery system having a micro-fluidic chamber. The micro-fluidic chamber includes a bottom substrate and a top cover, the top cover being spaced from the bottom substrate so as to define a height of the chamber. The one or more walls or fillings may be positioned in the chamber such that the walls or fillings define a fluid channel there between and such that the fluid channel extends from an inlet of the chamber to an outlet of the chamber. Each of the walls or fillings may have a height less than the height of the chamber so as to define a fluid gap between a top surface of each wall or filling and the top cover, and the dimensions of the walls or fillings and the chamber may be such that the fluid gap will be filled with liquid by capillary forces via the fluid channel when liquid is introduced into the fluid chamber.

In yet another embodiment a pressure sensor for use in a liquid medicament delivery system is provided. The pressure sensor includes a rigid bottom structure and a top cover, the top cover including a flexible membrane being spaced from the rigid bottom structure so as to define a height of a chamber. The one or more walls or fillings may be positioned in the chamber, the walls or fillings defining a fluid channel there between such that the fluid channel extends from an inlet of the chamber to an outlet of the chamber. Each of the walls or fillings may have a height less than the height of the chamber so as to define a fluid gap between a top surface of each wall or filling and the top cover and the dimensions of the walls or fillings and the chamber are such that the fluid gap will be filled with liquid by capillary forces via the fluid channel when liquid is introduced into the chamber. Furthermore, when there is no pressure difference between an external pressure of the chamber and an internal pressure of the chamber, the top cover remains flat, and when the external pressure of the chamber is less than the internal pressure, the top cover bulges outwards.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings where like structure is indicated with life reference numerals and in which:

DETAILED DESCRIPTION

Referring to FIGS. 1(a)-(c), an exemplary embodiment of a micro-fluidic chamber is illustrated. A circularly shaped fluid chamber 1 can comprise a bottom substrate 11 and a top cover 12. The top cover 12 may be spaced from the bottom substrate 11 by a certain height H1, thus defining an inner volume 14 of the chamber 1. In one embodiment, eight walls 13 may be arranged in the fluid chamber 1 (as best illustrated in FIG. 1(a)), and define a meander-like (e.g., bending, weaving or curving) fluid channel 2 that runs from an inlet 21 to an outlet 22 located on the opposite side of the chamber 1. Thus the inlet conduit 211 and the outlet conduit 221 can be fluidly connected by the fluid channel 2.

The height H2 of the walls 13 may be less than the overall height H1 of the chamber 1. As a result, there may be a fluid gap 3 between the top cover 12 and the upper surface 131 of the walls 13, with a height H3=H1−H2. The dimensions of the chamber and the walls, particularly the heights H1, H2, H3 may be chosen such that there are non-negligible capillary forces acting on a fluid 4 present in the micro-fluidic chamber 1. Fluid 4 in the fluid channel 2 may be dragged by said capillary forces into the fluid gap 3.

In one embodiment, the specific dimensions may depend on the liquid used. In another embodiment, the specific dimensions may additionally or alternatively depend on the properties of the surfaces of the top cover 12 and the top 131 of the walls 13. Such factors may eventually define the interface tensions between the liquid, surfaces, and the gas/air in the chamber, which then may define the effective capillary forces for a certain geometric setting of a micro-fluidic chamber. In one exemplary embodiments, where liquid medicaments are aqueous solutions, at least some surfaces, such as the surface of the top surface 131 of the wall 13 and the surface of the top cover 12 facing toward surface 131, may be hydrophilic, with a contact angle <90°. Such an embodiment may thereby increase the overall capillary effect. In another exemplary embodiment, where the liquid medicaments are aqueous solutions, the height H3 of the gap 3 may comprise between 20 and 200 μm. In another embodiment, the height H3 of the gap 3 may comprise between 50 and 150 μm.

In one embodiment, a diameter of a micro-fluidic chamber 1 may, for example, comprise between about 2 to 10 mm. In another embodiment, the fluid channels may comprise a width of, for example, 0.1 to 1 mm, while the height H2 of the walls 13 comprise between 0.25 to 5 mm, or alternatively, 0.5 and 1 mm. In yet another embodiment, the aspect ratio between the width of the fluid channel 2 and the height H2 can lie between 0.25 and 5, or alternatively, comprise about 1.

When a micro-fluidic chamber 1 according is filled through inlet 21 with a liquid 4, the liquid may flow essentially along the fluid channel 2. The capillary forces may then drag liquid 4 in the fluid channel 2 into the adjacent sections of the gap 3, thereby effectively supplanting air present in the gap. As it may be energetically more favorable for air to form spherical bubbles with minimum surface toward the hydrophilic surroundings, no or minimal air bubbles may remain in the gap 3.

Referring now to FIGS. 2(a)-(b), the first filling of a micro-fluidic chamber 1 of a liquid medicament delivery system 100 is illustrated. Specifically, in FIG. 2(a) an aqueous liquid 4 has flown downstream through inlet conduit 211 and inlet 21 into the fluid channel 2, and is currently at a position B. Due to the capillary forces in the gap 3, the liquid 4 flows into the sections 3.1, 3.2, 3.3, 3.4 of gap 3 adjacent to the fluid channel 2 already filled. In the gap, the surrounding still empty sections of the fluid channel 2, downstream of position B, limit the further flow of the liquid. Thus, the gap 3 filled section by section. Referring no to FIG. 2(b), at a later stage, the liquid 4 has proceeded in the fluid channel 2 to a position C. All sections of the gap 3 are filled except section 3.10, which has not yet come into contact with the liquid 4. As illustrated in FIGS. 2(a)-(b), no air remains in the part of the chamber that has already been filled by liquid. When the liquid finally reaches the outlet 22 and the outlet conduit 221, the micro-fluidic chamber may be completely filled with no or minimal air bubbles remaining in the chamber.

Air bubbles in the gap may be energetically less preferable than air bubbles in the fluid channel 2. As a consequence, air bubbles may not form in the gap 3 at a later stage, and if they do, they will migrate into the fluid channel 2. Air bubbles in the fluid channel 2, on the other hand, may not enter the gap 3 for energy reasons, but may be transported away by the liquid stream.

The shown capabilities of a micro-fluidic chamber 1 may be independent from its orientation in space. Since the capillary forces and interface tensions responsible for the smooth filling of the gap can be stronger than the gravitational force acting on the liquid, as well as the buoyancy force acting on the air bubbles in the liquid, the micro-fluidic chamber may be completely filled with liquid 4 independent on its orientation. Thus, the filling behavior of such a micro-fluidic chamber may become more predictable and reproducible.

Since the operational internal volume of a micro-fluidic chamber may be smaller than that of a hollow micro-fluidic chamber with similar dimensions, the dead volume—the portion of the fluid volume in a fluid system that can never be drained and eventually will be lost—may be considerably reduced.

Furthermore, the air bubbles that do enter the chamber through the inlet may be guided through the fluid channel to the outlet. Since the effective cross-sectional area of the fluid channel may be essentially constant over its length, the liquid flow may also be constant over its length, and does not drop at certain positions. Thus, bubbles may not be caught in the fluid chamber.

Figure 1:
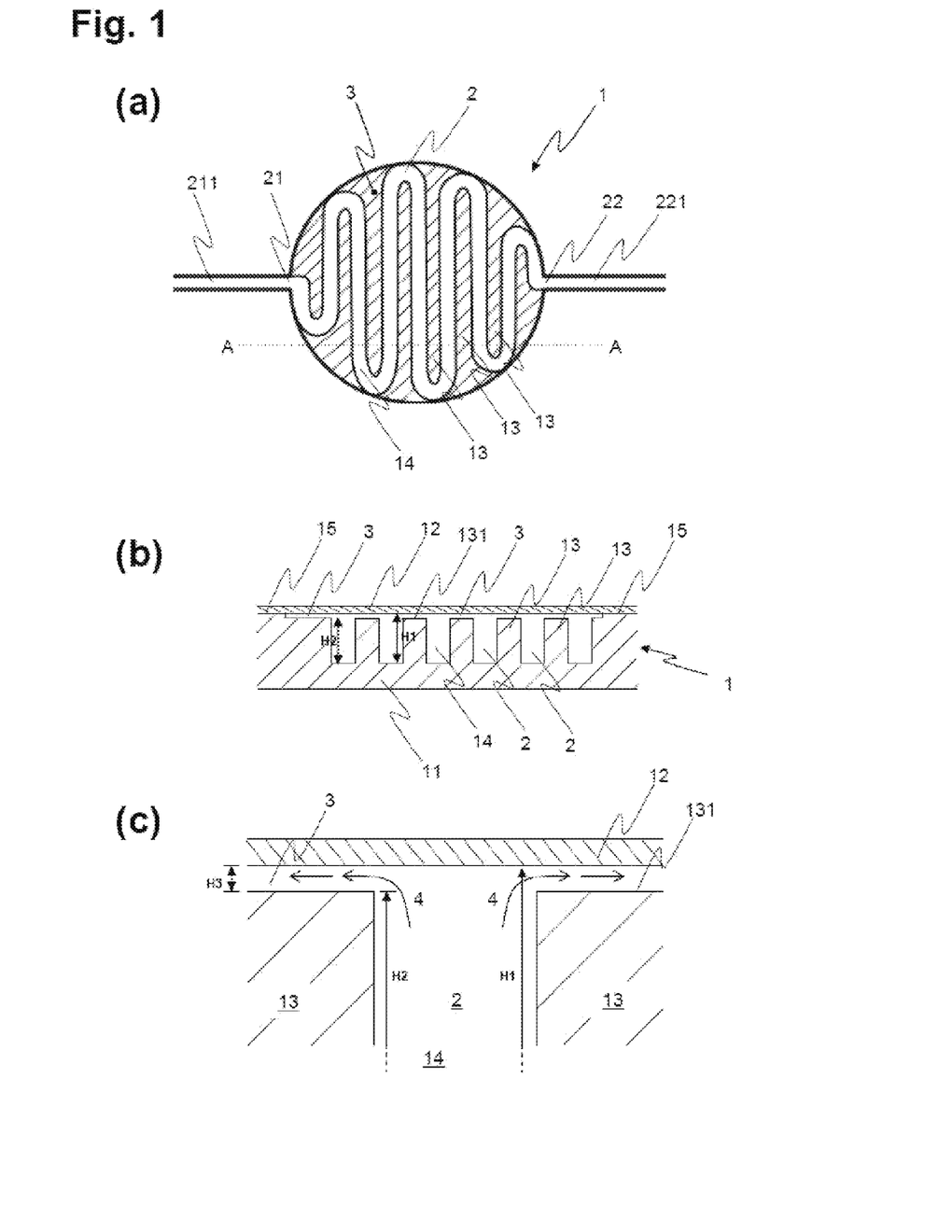
FIG. 1(a) schematically depicts a top view of a micro-fluidic chamber according to one or more embodiments shown and described herein.
FIG. 1(b) schematically depicts a cross-section along plane A-A of FIG. 1(a) according to one or more embodiments shown and described herein.
FIG. 1(c) depicts an enlarged view of a portion of FIG. 1(b) according to one or more embodiments shown and described herein.
Figure 2:
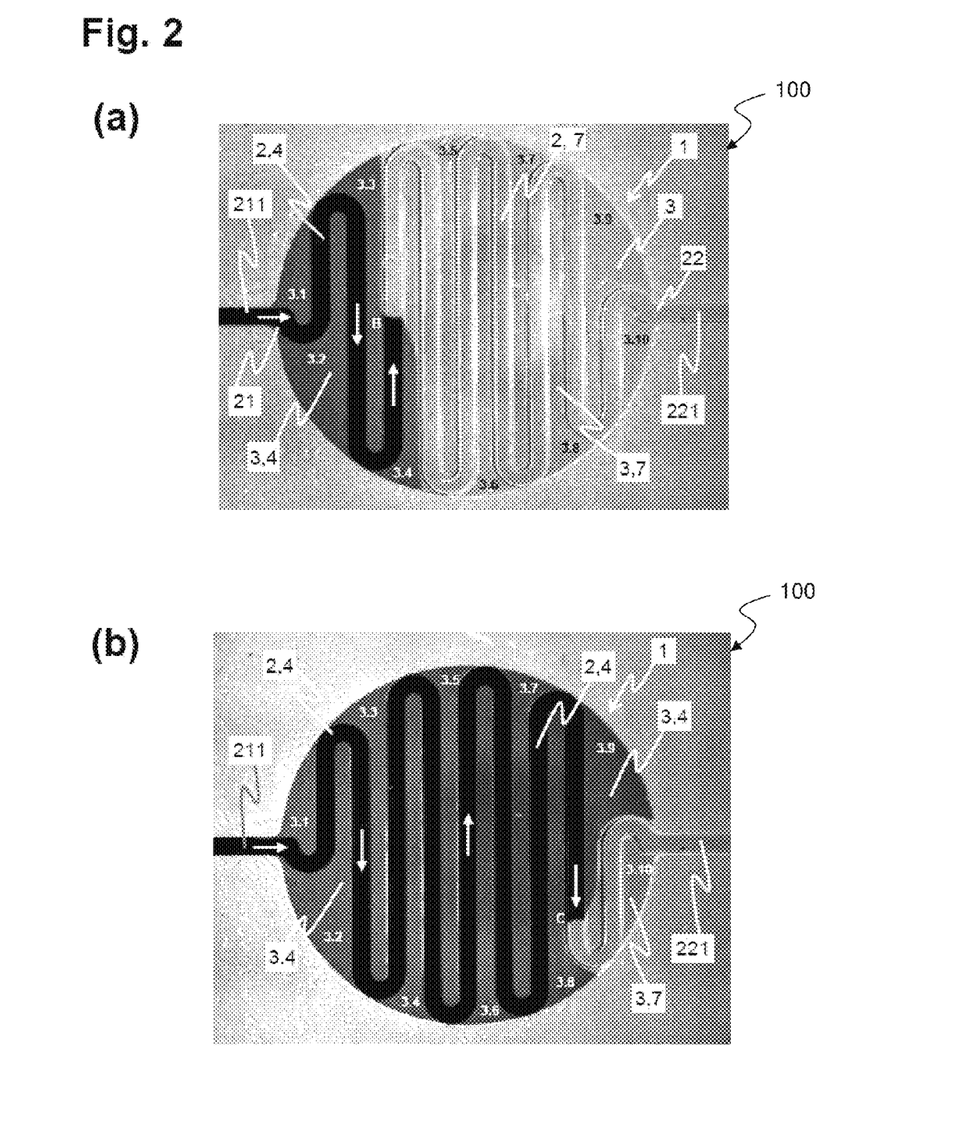
FIG. 2(a) the distribution of liquid in a real experiment during a first stage of the filling of the a micro-fluidic chamber according to one or more embodiments shown and described herein.
FIG. 2(b) the distribution of liquid in a real experiment during a second stage of the filling of the a micro-fluidic chamber according to one or more embodiments shown and described herein.

Still referring to FIGS. 1-2, a micro-fluidic chamber may have any other suitable shape as well as the specific design of the fluid channel in the chamber, both of which may depend on the specific application of the micro-fluidic chamber. For example, referring now to FIGS. 3(a)-(d), possible variants of micro-fluidic chambers are illustrated. Specifically, in the embodiment illustrated in FIG. 3(a), the meanders of the fluid channel 2 may be arranged in an elliptically shaped chamber 1, while in the embodiment illustrated in FIG. 3(b), the chamber 1 may comprise a substantially rectangular shape. In the embodiment illustrated in FIG. 3(c), a circularly shaped chamber 1 can comprise an alternative course of a meandering fluid channel 2.

Alternatively, instead of having a single fluid channel 2, the walls 13 of a micro-fluidic chamber may define two or more fluid channels within the chamber, extending from a common inlet to a common outlet. For example, such an embodiment of an exemplary micro-fluidic chamber 1 is illustrated in FIG. 3(d). In such an embodiment, an inlet conduit 211 may open towards the chamber 1 through a common inlet 21. The fluid channel may then split up into two separate fluid channels 2, 2', and may join again at a common outlet 22. In such an embodiment, constructive means such as flow barriers may be provided to ensure that during the filling procedure the chamber 1 is completely filled before the liquid flow proceeds further through the outlet 22.

A curved or meandering design of the fluid channel may be utilized in fluid chambers with larger base areas, since the longest possible distance between the fluid channel and an outer edge of the gap is relatively short. In addition, the meandering fluid channel can be used to limit the maximum flow through a fluidic system.

Figure 4:
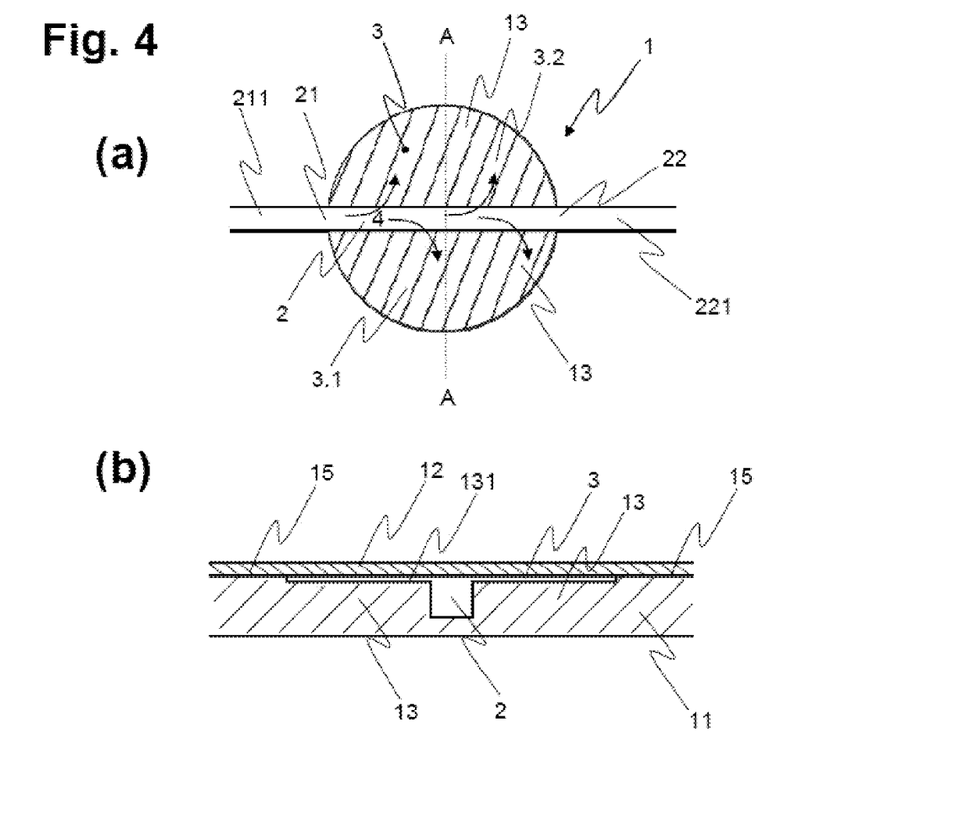
FIG. 4(a) depicts a top view of a micro-fluidic chamber with a straight fluid channel according to one or more embodiments shown and described herein.
FIG. 4(b) depicts the cross-section along plane A-A of FIG. 4(a) according to one or more embodiments shown and described herein.

In yet another embodiment, a straight fluid channel may be utilized in micro-fluidic chambers. For example, such an embodiment of a micro-fluidic chamber 1 comprising a straight fluid channel is illustrated in FIG. 4. In such an embodiment, a straight fluid channel 2, arranged in a circularly shaped chamber 1, may be in line with the inlet conduit 211 and the outlet conduit 221. Liquid 4 passing through the fluid channel 2 may be dragged into the two adjacent sections 3.1, 3.2 of the gap 3 on both sides of the fluid channel 2. Such an embodiment of a micro-fluidic chamber 1 may reduce the overall inner volume of the chamber 1 in relation to the area of the gap 3 and may also reduce flow resistance compared to a meander-shaped fluid channel.

Figure 3:
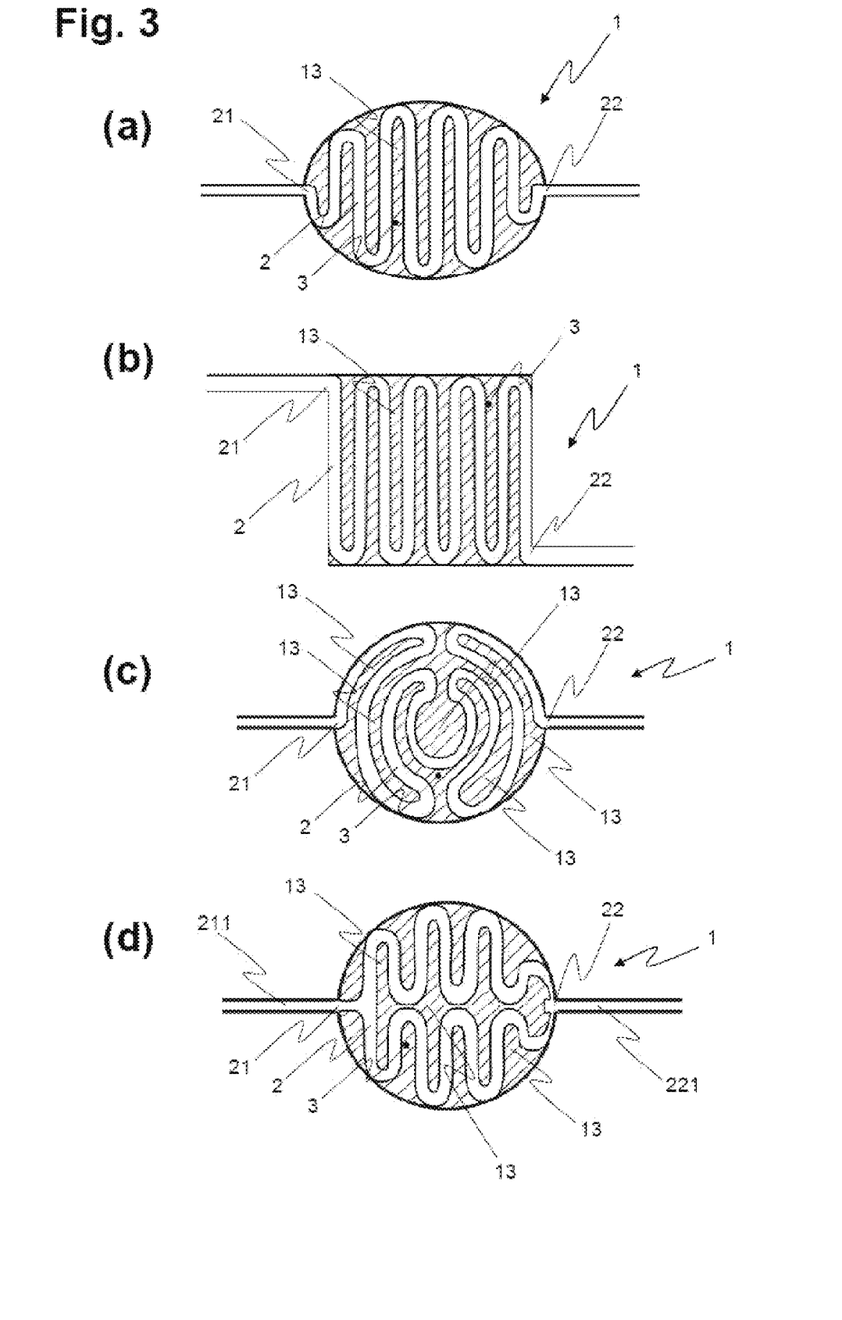
FIG. 3(a) depicts a micro-fluidic chamber according to one or more embodiments shown and described herein.
FIG. 3(b) depicts another micro-fluidic chamber according to one or more embodiments shown and described herein.
FIG. 3(c) depicts yet another micro-fluidic chamber according to one or more embodiments shown and described herein.
FIG. 3(d) depicts even yet another micro-fluidic chamber according to one or more embodiments shown and described herein.
Figure 5:
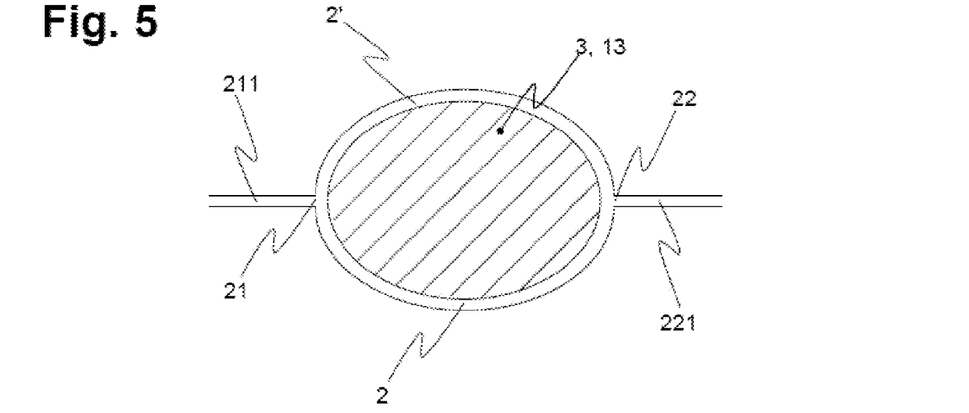
FIG. 5 depicts a micro-fluidic chamber with a single wall arranged in the centre of the chamber according to one or more embodiments shown and described herein.

Referring now to FIG. 5, yet another embodiment of a micro-fluidic device 1 is illustrated, wherein two fluid channels 2, 2' run from a common inlet 21 along the edge of the chamber 1 to a common outlet 22. A single wall or filling 13 may be arranged in the centre of the chamber 1. The resulting central gap 3 may thus be defined by the volume between the large circular top surface of the wall 13 and the top cover. Similar to the embodiment illustrated in FIG. 3(*d*), constructive barriers such as a flow barriers may be used to ensure a complete filling of the chamber.

Referring now to FIGS. 1-5, as discussed above, the fluid chamber 1 comprises a bottom structure 11 and a top cover 12, which may be sealed together in a sealing area 15 along an outer rim of the chamber 1. The bottom substrate 11 and the top cover 12 may comprise any suitable material or materials such as, for example, polymeric materials. Furthermore, any suitable method may be used to connect the two substrates 11, 12 such as, for example, thermal bonding, laser bonding, gluing etc.

In one embodiment, the walls 13 may be realized as an integral part of the bottom substrate 11. In such an embodiment, the fluid channel 2, and even the inlet and outlet conduits can, as an example, be produced by embossing the necessary void structures into a flat bottom structure 11. To obtain the necessary gap 3, one may arrange a thin spacer layer with height H3 between the bottom layer structure and the top layer 12 around the chamber, or may produce the gap together with the fluid channel and the walls in the embossing step. In an alternative embodiment, the micro-fluidic chambers may be manufactured via injection molding.

In one particular embodiment, the walls 13 may comprise separate filling structures, mounted onto a flat bottom layer 11. In such an embodiment, a filling body may be attached to a bottom layer, and then may be arranged between said bottom layer and a adjacent top layer in a sandwich-like manner.

Such micro-fluidic chambers may thereby be manufactured in large numbers and on continuous production lines which may, for example, reduce the effective costs per piece and increase their viable use as with for disposable products, such as for parts of an infusion pump device that are disposed after use for hygienic reasons.

In one embodiment, the micro-fluidic chamber may be used with pressure sensors for fluidic systems, such as, for example, for pressure sensors for miniaturized pump systems such as infusion pump devices for liquid medicaments. For example, a pressure sensor with a micro-fluidic chamber may comprise a rigid bottom structure 11 and a flexible, resilient membrane 120 as the top layer 12. When there is no pressure difference between the external pressure and the internal pressure of the fluidic system, the top layer membrane 120 may remain flat. In the case of a positive pressure difference, the membrane 120 may bulge outwards. The resulting displacement of the outer surface of the flexible membrane 120 then may be used to determine the current pressure difference. In the case of a negative pressure difference, where the flexible membrane 120 may be displaced inwards toward the chamber 1, the walls 13 may support the membrane 120, thereby avoiding an occlusion of the micro-fluidic chamber 1, or even damage of the membrane 120. In such embodiments, the pressure sensor with a micro-fluidic chamber may comprise reduced dead volume.

In an alternative embodiment of a micro-fluidic chamber for use in a pressure sensor, the roles of the bottom substrate and the top layer may be reversed. In such a variant, the top layer may comprise a rigid structure, while the bottom substrate may comprise a flexible, resilient membrane. Thus, the walls or fillings may protrude from the flexible membrane. To measure the pressure in the fluid system, the deformation of the flexible bottom structure may be measured.

Figure 6:
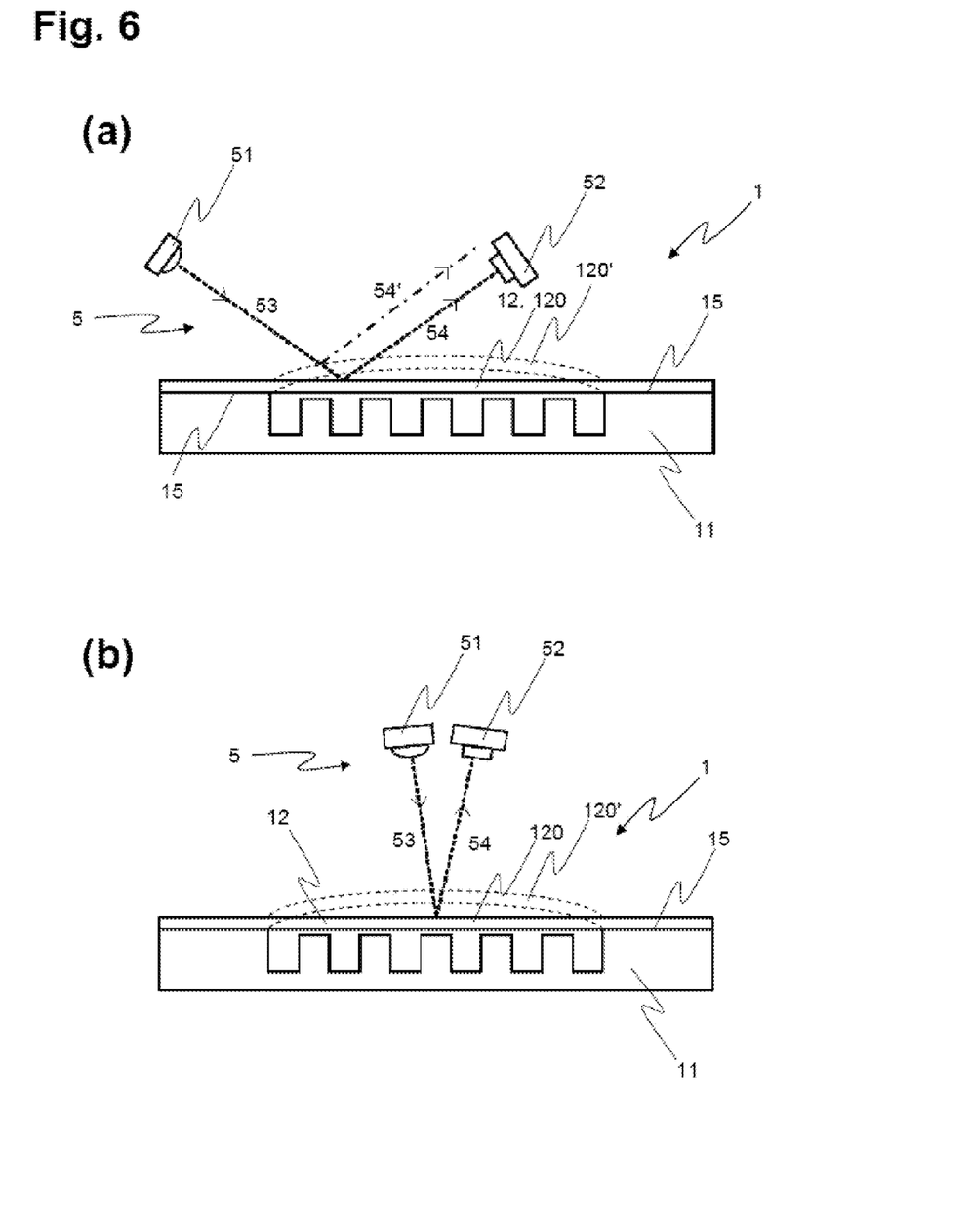
FIG. 6(a) depicts an optical detection scheme for the measurement of the displacement of the top membrane of a micro-fluidic chamber of a pressure sensor according to one or more embodiments shown and described herein.
FIG. 6(b) depicts another optical detection scheme for the measurement of the displacement of the top membrane of a micro-fluidic chamber of a pressure sensor according to one or more embodiments shown and described herein.

In such embodiments, various systems may be utilized to measure the displacement of the flexible membrane 120. For example, referring to FIGS. 6(*a*)-(*b*), two possible embodiments of detection systems 5 based on optical principles are illustrated. Specifically, FIG. 6(*a*) illustrates a cross-section of a micro-fluidic chamber 1 similar to that illustrated in FIG. 1. The top cover 12 may be realized as a flexible, resilient membrane layer 120, sealed 15 to the basic structure 11 along the outer rim of the chamber 1. An optical detection system 5 may comprise a light emitting device 51, such as, for example, a light emitting diode (LED) or a laser diode, and a photo sensor 52, such as, for example, a photo diode or a photo transistor. The light emitting device 51 and the photo sensor 52 may be arranged such that an incident light beam 53 emitted by the light emitting device 51 is reflected 54 by the surface of the top cover 12 toward the photo sensor 52, where it may be detected. In one embodiment, the top cover may be metal vapor coated to increase reflection. When the top cover 12 bulges under a positive pressure difference (as illustrated as dashed lines 120'), the reflected light beam 54' does not impinge any longer on photo sensor 52. In such an embodiment, the detection system 5 may thereby deliver a binary on/off signal correlated to a certain pressure threshold, which may be used by a control unit of an infusion pump system. Such a system may thereby detect occlusion in a fluid line. In another embodiment, to achieve a higher resolution in the pressure values, a sensor array may be used instead of a single sensor. Such an embodiment may be utilized where the pressure values are used by a control unit to calculate the current flow of liquid and the administered dose of liquid medicament.

Referring now to FIG. 6(*b*), another embodiment of an optical detection system is illustrated wherein the light emitting device 51 and the photo sensor 52 are arranged in such a way that the reflected light beam 54 will fall onto the photo sensor 52 independent of a displacement of the top cover membrane 120, 120'. The position of the surface of the top cover 12 may be determined by analyzing the amplitude of the reflected light 54, which depends on the length of the combined light path 52, 54.

Figure 7:
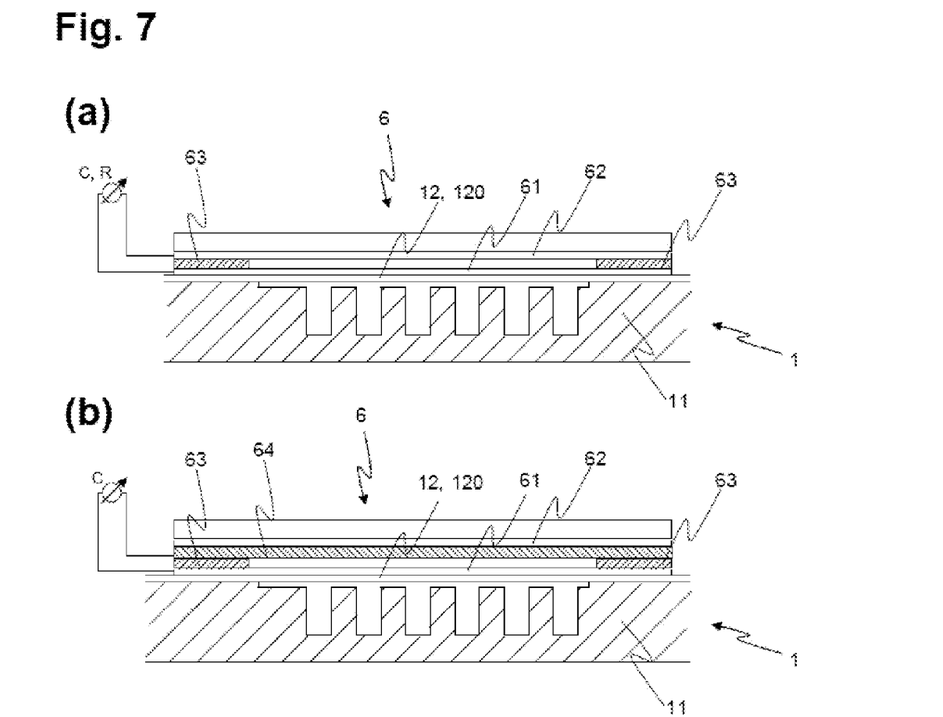
FIG. 7(a) depicts a capacitance detection scheme for the measurement of the displacement of the top membrane of a micro-fluidic chamber of a pressure sensor according to one or more embodiments shown and described herein.
FIG. 7(b) depicts another capacitance detection scheme for the measurement of the displacement of the top membrane of a micro-fluidic chamber of a pressure sensor according to one or more embodiments shown and described herein.

Referring now to FIGS. 7(*a*)-(*b*), additional embodiments of a pressure sensor with a micro-fluidic chamber 1 are illustrated wherein the displacement of the flexible membrane 120 is determined by measuring a capacitance. For example, referring to FIG. 7(*a*), a first capacitor electrode 61, for example a thin metal foil, may be arranged adjacent to the flexible top cover membrane 120. Alternatively the membrane 120 itself can comprise a capacitor electrode 61, for example by coating it with a conducting material.

Still referring to FIG. 7, insulating spacer elements 63 may define a distance between said first capacitor electrode 61 and a second capacitor electrode 62, located on top of the spacer elements 63 and the first capacitor electrode 61. The two capacitor electrodes 61, 62 may be electrically isolated from each other, and thus act as a capacitor with a capacitance C, which can be measured. With increasing internal pressure in the micro-fluidic chamber 1, the flexible, resilient membrane 120 may bulge outwards. The first capacitor electrode 61 may then be displaced towards the second capacitor electrode 62. As a result, the capacitance C increases, which can be detected and used to determine the deformation of the membrane 12, 120, and the internal pressure in the chamber 1 causing said deformation, respectively.

As the internal pressure increases, the first capacitor electrode 61 may eventually touch the second capacitor electrode 61, and the ohmic resistance R between the two layers drops to zero. This event may also be detected by suitable electronic means, and can be used—in addition or as an alternative to the capacitance—as an input for a control system of an infusion pump device.

Referring now to FIG. 7(b), in another embodiment, a capacitive detection system 6 is illustrated wherein an additional insulating layer 64 is arranged between the spacer elements 63 and the second capacitor electrode 62. Said additional layer 64 may inhibit a short-circuit between the two capacitor electrodes 61, 62, which can be preferable, depending on the used capacitance measurement circuitry.

In yet another embodiment, the second capacitor electrode 62 may be located on the opposite side of the chamber 1, below the bottom structure, or integrated into the bottom structure.

In another embodiment, micro-fluidic chambers may be utilized in degassing devices for fluidic systems, such as in infusion pump devices for liquid medicaments. For example, referring to FIG. 8, one exemplary embodiment of a degassing device with a micro-fluidic chamber 1 is illustrated. The degassing device with a micro-fluidic chamber 1 may comprise a rigid bottom structure 11 and a gas-permeable membrane 121 as the top layer 12. In one embodiment, the gas permeable membrane 121 may comprise a relatively high stiffness. Such an embodiment may be used, for example, in a fluidic system of an infusion pump device, where it can be arranged in different positions along the liquid stream.

Figure 8:
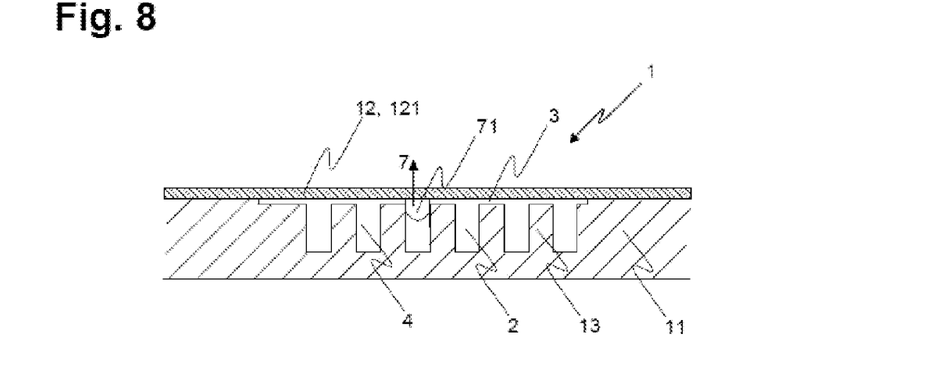
FIG. 8 depicts an embodiment of a degassing device with a micro-fluidic chamber according to one or more embodiments shown and described herein.

As discussed above, prior to the first use, the degassing device with a micro-fluidic chamber can be filled without air bubbles, independent on the orientation of the device in space, due to the characteristics of the micro-fluidic chamber 1. Then, during the operational use of the fluidic system, an air bubble 71 may be flushed into the degassing device, along with the stream of liquid 4, and it can move along the meandering fluid channel 2. The interface tensions may inhibit the entrance of even of small air bubbles into the gap 3. However, the air 7 in the air bubble 71 may nonetheless be able to pass the gas-permeable membrane 121, provided that there is a sufficiently high difference of the partial pressure of the gas between the fluidic system and the other side of the gas permeable membrane. For an air bubble in the fluidic system the partial gas pressure may be substantially similar to the liquid pressure.

When the surface characteristics of the walls 13, the bottom structure 11, and the gas permeable membrane 121 are selected, it may become energetically preferable for an air bubble 71 to be in contact with the gas permeable membrane 121. However, in another embodiment, it is also possible that an air bubble may be drained through the gas permeable membrane indirectly, via the liquid, since the gas can be solved in the liquid. This effect may assist in the removal of small air bubbles with a large surface compared to their volume. Although the air bubbles 71 may not enter the gap 3, gas 7 solved in the liquid may migrate into the gap 3, and permeate through the membrane 121. Thus a degassing device with a micro-fluidic chamber 1 may have a larger effective membrane surface compared to the operational internal volume, which may correlate to a faster dissolution of air bubbles and reduced dead volume.

In one embodiment, to provide the air bubbles more time to drain through the gas-permeable membrane, while at the same time maintaining a sufficiently high through-put of liquid, a degassing device may be combined with a bubble trap.

Figure 9:
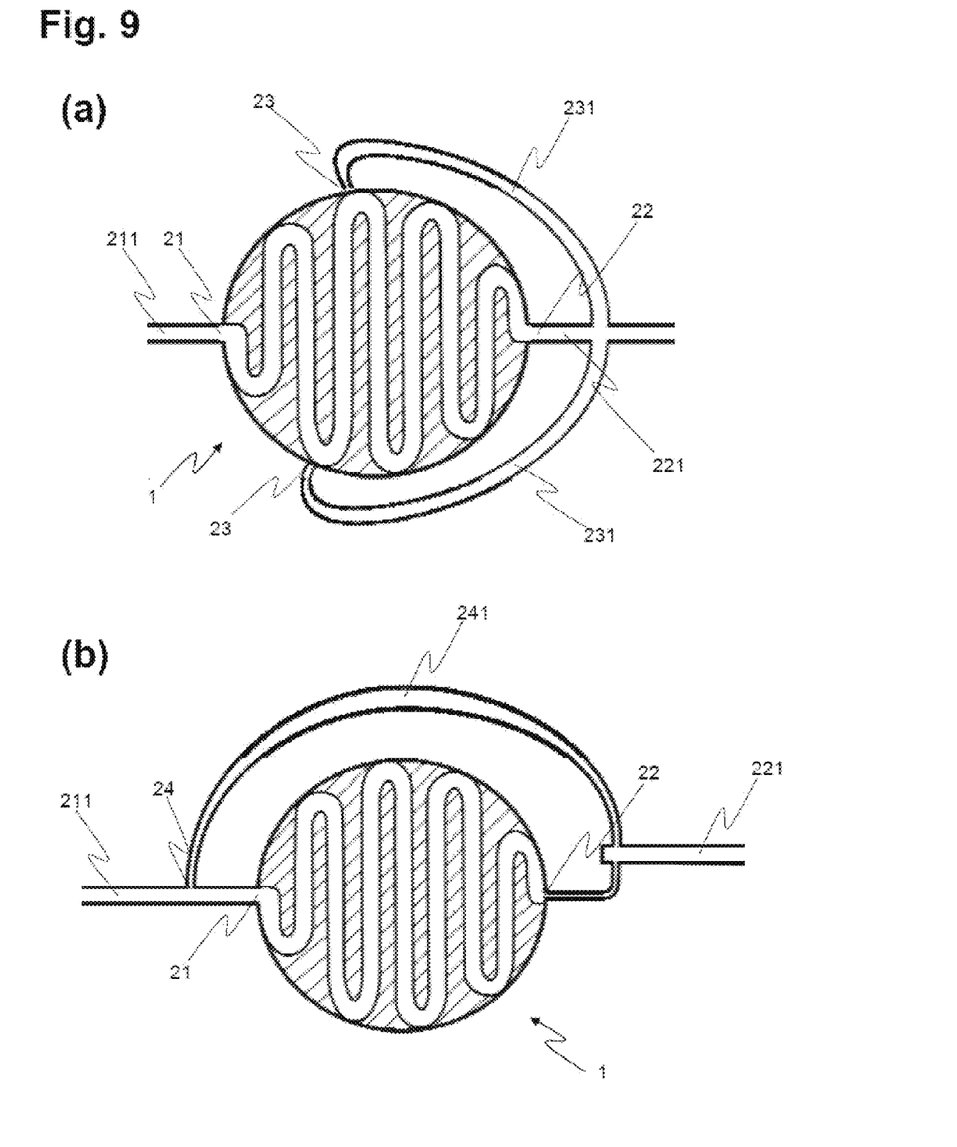
FIG. 9(a) depicts a micro-fluidic chamber with additional outlets along the fluidic channel in the chamber, providing bubble-trap capabilities, according to one or more embodiments shown and described herein.
FIG. 9(b) depicts a micro-fluidic chamber with a bypassing additional conduit according to one or more embodiments shown and described herein.

Referring now to FIG. 9, two additional exemplary embodiments of degassing devices are illustrated. Specifically, as illustrated in FIG. 9(a), two additional outlet openings 23 may be located at different positions along the meandering fluid channel 2, from which additional outlet conduits 231 branch off. Downstream of the main outlet 22 the outlet conduits 221, 231 may converge again to a common outlet conduit. The additional outlet openings 23 may be smaller than the main outlet opening 22. In one particular embodiments, the width of the narrow outlets 23 may be 50% or less of the width of the fluid channel 2. For an air bubble with certain dimensions, this may be energetically less favorable to enter the narrow outlet 23, due to the interface tensions, than to stay in the comparably wide fluid channel 2. There, the bubbles may continue to drain through the gas-permeable membrane. Thus, the chamber 1 may act as a bubble trap. Since three outlets 23, 22 are available, the through-put of liquid through the degassing device may be increased.

Referring now to FIG. 9(b), another exemplary embodiment of a degassing device with a micro-fluidic chamber 1 is illustrated comprising an additional conduit 241 bypassing the chamber 1. The bypass conduit 241 may directly connect the inlet conduit 221 to the outlet conduit 221. In one embodiment, the width of the inlet 24 of the bypass conduit 241 may be much smaller, such as, 50% or less, than the width of the inlet conduit 211. In such an embodiment, it may thereby be not favorable for an air bubble to enter the inlet 24 and bypass conduit 241, and the air bubble may enter the degassing device, where it can dissolve. As illustrated in the embodiment seen if FIG. 9(b), the outlet 22 of the micro-fluidic chamber 1 may be comprise a relatively narrower embodiment. In such an embodiment, it may act as a bubble trap, keeping any air bubble in the degassing device. In one particular embodiment, the width of the outlet 22 may be 50% or less of the width of the fluid channel 2. To ensure that both the bypass conduit 241 and the micro-fluidic chamber 1 are completely filled during the first filling procedure, a flow barrier or a similar means may additionally be used.

In one exemplary embodiment, the additional outlets 231 in FIG. 9(a) and the bypass 241 in FIG. 9(b) may also useful in a pressure sensor, in order to increase the overall capacity of the fluidic system.

It should now be appreciated that micro-fluidic chambers as disclosed herein may provide a smaller dead volume that may be fillable without air remaining in the chamber. Such micro-fluidic chambers may be filled essentially independent on its orientation in space such that it may be provided as a pressure sensor for use in a fluidic system, particularly in an infusion pump device for liquid medicaments. Degassing devices may also be provided comprising the micro-fluidic chambers for use in a fluidic system, and particularly, in an infusion pump device for liquid medicaments. Furthermore, infusion pump devices or parts of an infusion pump device, and liquid medicament delivery systems can comprise such micro-fluidic chambers, such as pressure sensor and/or a degassing device.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed:

1. A micro-fluidic chamber for use in a liquid medicament delivery system, the micro-fluidic chamber comprising:
   a bottom substrate and a top cover, the top cover being spaced from the bottom substrate so as to define a height of the micro-fluidic chamber;
   wherein, two or more walls or fillings are positioned in the micro-fluidic chamber, the walls or fillings forming a fluid channel between the walls or fillings, the fluid channel extending from an inlet conduit connected to an inlet of the micro-fluidic chamber to an outlet conduit connected to an outlet of the micro-fluidic chamber;
   wherein, each of the walls or fillings has a height less than the height of the micro-fluidic chamber so as to define a fluid gap between a top surface of each wall or filling and the top cover; and
   wherein, the dimensions of the walls or fillings and the micro-fluidic chamber are such that the fluid gap will be filled with liquid by capillary forces via the fluid channel when liquid is introduced into the micro-fluidic chamber;
   wherein, the top cover comprises a gas-permeable membrane which allows gas to freely pass through the gas-permeable membrane and prevents liquid from passing through the gas-permeable membrane.

2. The micro-fluidic chamber of claim 1, wherein a height of the fluid gap is from 0.02 to 0.2 mm.

3. The micro-fluidic chamber of claim 2, wherein a height of the fluid gap is from 0.05 and 0.15 mm.

4. The micro-fluidic chamber of claim 1, wherein the top cover comprises a flexible membrane.

5. The micro-fluidic chamber of claim 1, wherein at least one of a part of the surface of the bottom structure, the walls, and the top cover facing toward an inner volume of the micro-fluidic chamber is hydrophilic.

6. The micro-fluidic chamber of claim 1, wherein the fluid channel comprises a meander-like shape.

7. The micro-fluidic chamber of claim 1, wherein the fluid channel extends uninterrupted from the inlet conduit to the outlet conduit.

8. A pressure sensor for use in a liquid medicament delivery system, the pressure sensor comprising:
   a rigid bottom structure and a top cover, the top cover comprising a flexible, resilient membrane being spaced from the rigid bottom structure so as to define a height of a chamber;
   wherein, two or more walls or fillings are positioned in the chamber, the walls or fillings forming a fluid channel between the walls or fillings, the fluid channel extending from an inlet conduit connected to an inlet of the micro-fluidic chamber to an outlet conduit connected to an outlet of the micro-fluidic chamber;
   wherein, each of the walls or fillings has a height less than the height of the chamber so as to define a fluid gap between a top surface of each wall or filling and the top cover;
   wherein, the top cover comprises a gas-permeable membrane which allows gas to freely pass through the gas-permeable membrane and prevents liquid from passing through the gas-permeable membrane;
   wherein, the dimensions of the walls or fillings and the chamber are such that the fluid gap will be filled with liquid by capillary forces via the fluid channel when liquid is introduced into the chamber; and
   wherein, when there is no pressure difference between an external pressure of the chamber and an internal pressure of the chamber, the top cover remains flat and when the external pressure of the chamber is less than the internal pressure, the top cover bulges outwards.

9. The pressure sensor of claim 8 wherein, wherein a height of the fluid gap is from 0.02 to 0.2 mm.

10. The pressure sensor of claim 9 wherein, wherein a height of the fluid gap is from 0.05 and 0.15 mm.

11. The pressure sensor of claim 8 wherein, a detection system is arranged to measure a deformation of the top cover of the chamber.

12. The pressure sensor of claim 8 wherein, wherein at least one of a part of the surface of the rigid bottom structure, the walls, and the top cover facing toward an inner volume of the micro-fluidic chamber is hydrophilic.

13. The pressure sensor of claim 8, wherein the fluid channel comprises a meander-like shape.

14. The pressure sensor of claim 8, wherein the fluid channel extends uninterrupted from the inlet conduit to the outlet conduit.

* * * * *

UNITED STATES PATENT AND TRADEMARK OFFICE
CERTIFICATE OF CORRECTION

| | | |
|---|---|---|
| PATENT NO. | : 9,603,998 B2 | Page 1 of 3 |
| APPLICATION NO. | : 12/877569 | |
| DATED | : March 28, 2017 | |
| INVENTOR(S) | : Andreas Geipel et al. | |

It is certified that error appears in the above-identified patent and that said Letters Patent is hereby corrected as shown below:

In the Specification

Column 1, Line 38:
"sion pump devices may be limited in order not be evident"
Should read:
--sion pump devices may be limited in order not to be evident--;

Column 2, Line 22:
"tioning pump systems. However, air bubbles in the in the"
Should read:
--tioning pump systems. However, air bubbles in the--;

Column 2, Line 36:
"solved in the liquid, can leave the fluidic system by perme-"
Should read:
--dissolved in the liquid, can leave the fluidic system by perme- --;

Column 5, Line 24:
"fluidic chamber. In one exemplary embodiments, where"
Should read:
--fluidic chamber. In one exemplary embodiment, where--;

Column 5, Line 44:
"When a micro-fluidic chamber 1 according is filled"
Should read:
--When a micro-fluidic chamber 1 accordingly is filled--;

Signed and Sealed this
Fifth Day of December, 2017

Joseph Matal
*Performing the Functions and Duties of the*
*Under Secretary of Commerce for Intellectual Property and*
*Director of the United States Patent and Trademark Office*

Column 5, Line 63:
"liquid. Thus, the gap 3 filled section by section. Referring no"
Should read:
--liquid. Thus, the gap 3 filled section by section. Referring now--;

Column 7, Line 24:
"constructive barriers such as a flow barriers may be used to"
Should read:
--constructive barriers such as a flow barrier may be used to--;

Column 7, Line 50:
"bottom layer and a adjacent top layer in a sandwich-like"
Should read:
--bottom layer and an adjacent top layer in a sandwich-like--;

Column 9, Line 57:
"inhibit the entrance of even of small air bubbles into the gap"
Should read:
--inhibit the entrance of even small air bubbles into the gap--;

Column 10, Line 28:
"particular embodiments, the width of the narrow outlets 23"
Should read:
--particular embodiment, the width of the narrow outlets 23--;

Column 10, Line 50:
"the micro-fluidic chamber 1 may be comprise a relatively"
Should read:
--the micro-fluidic chamber 1 may comprise a relatively--;

Column 10, Line 60:
"in FIG. 9(a) and the bypass 241 in FIG. 9(b) may also useful"
Should read:
--in FIG. 9(a) and the bypass 241 in FIG. 9(b) may also be useful--;

In the Claims

Column 12, Claim 9, Line 40:
"9. The pressure sensor of claim 8 wherein, wherein a"
Should read:
--9. The pressure sensor of claim 8 wherein, a--;

Column 12, Claim 10, Line 42:
"10. The pressure sensor of claim 9 wherein, wherein a"
Should read:
--10. The pressure sensor of claim 9 wherein, a--; and Column 12, Claim 12, Line 47:
"12. The pressure sensor of claim 8 wherein, wherein at"
Should read:
--12. The pressure sensor of claim 8 wherein, at--.